(12) United States Patent
Koh

(10) Patent No.: US 7,336,999 B1
(45) Date of Patent: Feb. 26, 2008

(54) MEANS TO CHECK THE VALIDITY OF HEART FAILURE SURROGATE PARAMETERS FROM EVOKED RESPONSE USING 3-D ACCELEROMETER QUEUE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 262 days.

(21) Appl. No.: 11/080,219

(22) Filed: Mar. 14, 2005

(51) Int. Cl.
*A61N 1/37* (2006.01)

(52) U.S. Cl. .......................... 607/27; 600/510

(58) Field of Classification Search ............... None
See application file for complete search history.

(56) References Cited

U.S. PATENT DOCUMENTS

| | | | |
|---|---|---|---|
| 4,686,988 A | 8/1987 | Sholder | 128/419 PT |
| 4,969,467 A | 11/1990 | Callaghan et al. | 128/419 PG |
| 5,350,410 A | 9/1994 | Kleks et al. | 607/28 |
| 5,431,689 A | 7/1995 | Weinberg et al. | 607/14 |
| 5,466,254 A | 11/1995 | Helland | 607/123 |
| 6,101,414 A | 8/2000 | Kroll | 607/14 |
| 6,101,416 A | 8/2000 | Sloman | 607/28 |
| 6,243,606 B1 | 6/2001 | Mann et al. | 607/14 |
| 6,259,950 B1 | 7/2001 | Mann et al. | 607/28 |
| 6,263,244 B1 | 7/2001 | Mann et al. | 607/28 |
| 6,285,908 B1 | 9/2001 | Mann et al. | 607/28 |
| 6,311,089 B1 | 10/2001 | Mann et al. | 607/30 |
| 6,345,201 B1 | 2/2002 | Sloman et al. | 607/28 |
| 6,434,428 B1 | 8/2002 | Sloman et al. | 607/28 |
| 6,456,881 B1 | 9/2002 | Bornzin et al. | 607/27 |
| 6,456,882 B1 | 9/2002 | Schloss | 607/28 |
| 6,519,493 B1 | 2/2003 | Florio et al. | 607/9 |
| 6,572,557 B2 | 6/2003 | Tchou et al. | 600/483 |
| 6,658,292 B2 | 12/2003 | Kroll et al. | 607/19 |
| 6,975,904 B1 * | 12/2005 | Sloman | 607/28 |
| 2005/0033368 A1 * | 2/2005 | Fishler et al. | 607/9 |

FOREIGN PATENT DOCUMENTS

EP  1 118 307 A1  7/2001

OTHER PUBLICATIONS

Karagoz, Tevfik et al., "The Influence of Mental and Physical Stress on the Autocapture Function in Children," *Journal of Interventional Cardiac Electrophysiology* 9, 43-48, 2003.

* cited by examiner

*Primary Examiner*—Kristen D. Mullen

(57) ABSTRACT

In one implementation, a method is provided for detecting heart failure which includes retrieving a three-dimensional posture template corresponding to a normal evoked response. The method further includes capturing an intracardiac electrogram of an evoked response and detecting a three-dimensional posture corresponding with the intracardiac electrogram. The detected three-dimensional posture and the three-dimensional posture template are compared. The captured intracardiac electrogram is used for heart failure trend analysis if the comparison of the detected three-dimensional posture and the three-dimensional posture template indicates a same posture.

23 Claims, 7 Drawing Sheets

MEANS TO CHECK THE VALIDITY OF HEART FAILURE SURROGATE PARAMETERS FROM EVOKED RESPONSE USING 3-D ACCELEROMETER QUEUE

BACKGROUND

Implantable pacemakers are capable of sensing the evoked response of a heart and delivering of pacing therapy if the heart fails. In heart failure, as the heart weakens, the morphology of the evoked response changes.

In certain types of heart failure, such as congestive heart failure or CHF, the change in the morphology of the evoked response can occur rapidly, or slowly, over time. Thus, analysis of the morphology and parameters of the evoked response, and the behavior such over time, is useful in predicting heart failure. If heart failure is indicated, treatment such as an alert system, medication delivery for example by an implantable pump, V-V timing control, etc. can be administered. Various devices and methods exist for analyzing the evoked response of a patient's heart as an indicator of cardiac health. Examples are found in European Patent Application EP 1 111 307 A1, by Fishler et al., filed Jan. 18, 2001, entitled AN IMPLANTABLE CARDIAC DEVICE FOR AND METHOD OF MONITORING PROGRESSION OR REGRESSION OF HEART DISEASE, and U.S. application Ser. No. 09/487,858, filed Jan. 1, 2000, both herein incorporated by reference in their entireties.

The morphology of the evoked response, however, also changes in response to patient posture. Thus, the evoked response morphology without considering posture can be unreliable as an indicator of heart failure.

If the evoked response morphology is to be successful as an indicator of heart failure, what is needed is a method and device capable of ensuring the validity of heart failure surrogate parameters from an evoked response.

SUMMARY

In one implementation, a method is provided for detecting heart failure which includes retrieving a three-dimensional posture template corresponding to a normal evoked response. The method further includes capturing an intracardiac electrogram of an evoked response and detecting a three-dimensional posture corresponding with the intracardiac electrogram. The detected three-dimensional posture and the three-dimensional posture template are compared. The captured intracardiac electrogram is used for heart failure trend analysis if the comparison of the detected three-dimensional posture and the three-dimensional posture template indicates a same posture. In some implementations, the detection of the three-dimensional posture is accomplished with a three-dimensional accelerometer.

In certain implementations, if the comparison of the detected three-dimensional posture and the retrieved three-dimensional posture indicate a different posture, the intracardiac electrogram is re-captured and the corresponding three-dimensional posture is re-detected for comparison with the three-dimensional posture template.

In one implementation, a method for detecting heart failure is provided which includes storing a normal evoked response parameter of a patient and storing patient position associated with the normal evoked response parameter. An evoked response parameter is detected along with a patient position corresponding to the detected evoked response. The detected patient position is compared with the stored patient position. The detected evoked response parameter is included in heart failure trend analysis if the detected patient position indicates a same posture as the stored patient position associated with the normal evoked response.

In certain implementations, the method includes compensating the detected evoked response parameter prior to including the detected evoked response parameter in heart failure trend analysis if the detected patient position indicates a different posture than the stored patient position associated with the normal evoked response. Some implementations include re-detecting the evoked response parameter and re-detecting the patient position corresponding with the re-detected evoked response parameter if the comparison of the detected patient position and the stored patient position indicates a different posture.

In certain implementations, the method includes storing a patient position corresponding to a normal evoked response parameter for multiple different postures. The detected evoked response parameter may be associated with one of the stored normal evoked response parameters that has a same posture associated with it.

In one embodiment, an implantable cardiac stimulation device is provided having a controller, memory, and at least one electrode capable of sensing and communicating an evoked response to the controller. The implantable cardiac stimulation device may include a three-dimensional position sensor, such as a three-dimensional accelerometer, which is adapted to provide signals to the controller. The controller has an executable instruction set which may include storing in the memory a normal evoked response parameter of a patient and storing in the memory a patient position associated with the normal evoked response parameter. In this embodiment, the executable instruction set includes detecting an evoked response parameter and detecting a patient position corresponding to the detected evoked response. The executable instruction set also include comparing the detected patient position with the stored patient position and including the detected evoked response parameter in heart failure trend analysis if the detected patient position indicates a same posture as the stored patient position associated with the normal evoked response.

In further embodiments the executable instruction set includes storing a patient position corresponding to a normal evoked response parameter for multiple different postures. It may also include associating the detected evoked response parameter with the stored normal evoked response parameter if the detected stored patient position indicates a same posture as the stored normal evoked response parameter.

In certain embodiments the executable instruction set may include re-detecting the evoked response parameter and re-detecting the patient position corresponding with the re-detected evoked response parameter if the comparison of the detected patient position and the stored patient position indicates a different posture. In some embodiments, the executable instruction set may include compensating the detected evoked response parameter prior to including the detected evoked response parameter in heart failure trend analysis if the detected patient position indicates a different posture than the stored patient position associated with the normal evoked response.

In another embodiment, an implantable cardiac pacemaker device is provided for detecting heart failure which includes a means for ensuring the validity of heart surrogate parameters from an evoked response using a three-dimensional accelerometer queue. The means for ensuring the validity of the heart surrogate parameters may further include a means for storing a template posture based on a three-dimensional accelerometer measurement, the template posture corresponding to a normal evoked response parameter and a means for periodically comparing a current posture based on the three-dimensional accelerometer queue with the template posture to verify whether an evoked response parameter corresponding to the current posture is valid for use in heart failure trend analysis.

DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
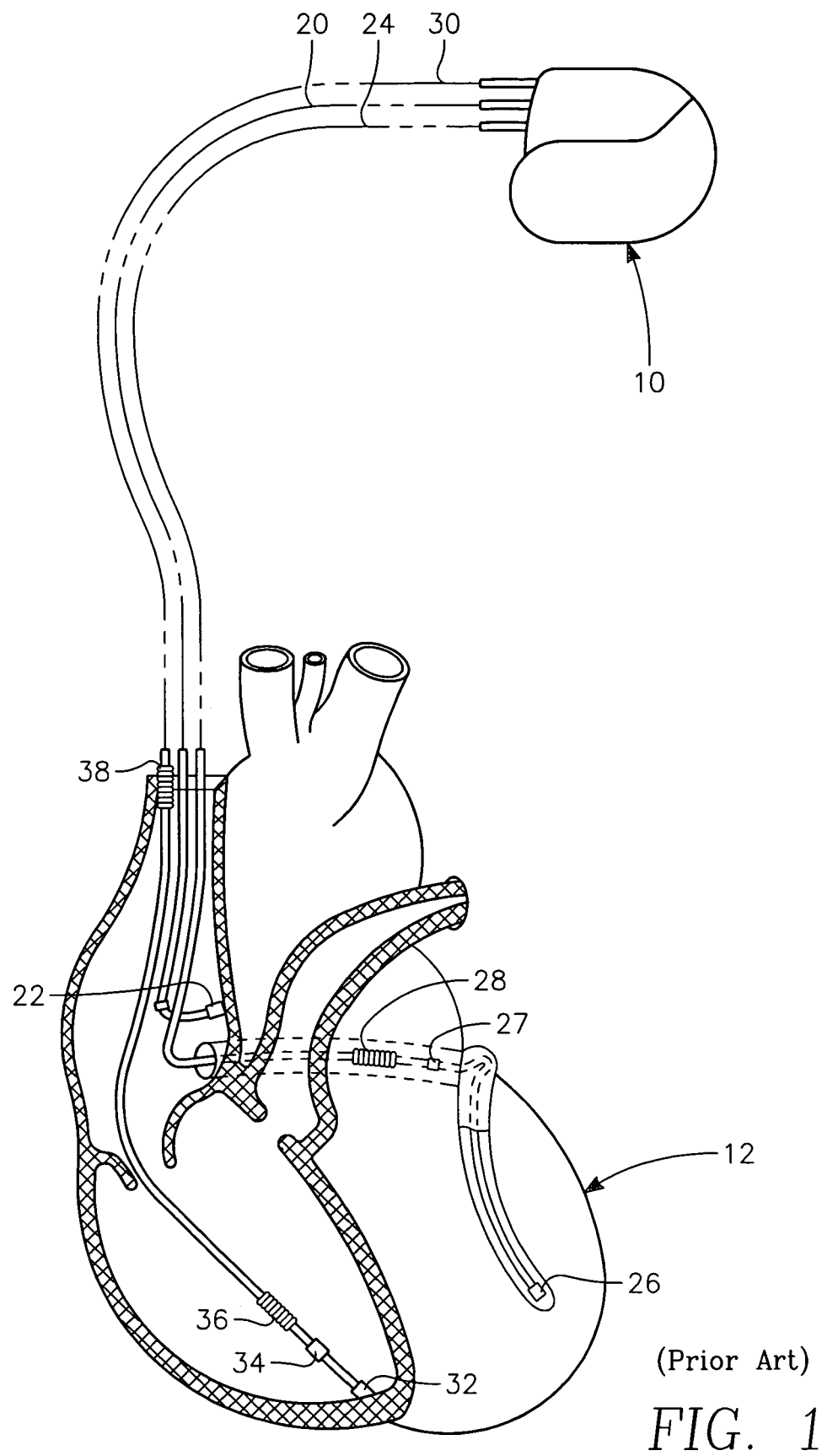
FIG. 1 shows a conventional stimulation device in electrical communication with a patient's heart by way of three leads suitable for delivering multi-chamber stimulation and shock therapy.

FIG. 1 shows a conventional stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage, and an atrial ring electrode 23. To sense left atrial and ventricular cardiac signals and to provide left chamber pacing therapy, the stimulation device 10 is coupled to a "coronary sinus" lead 24 designed for placement in the "coronary sinus region" via the coronary sinus or for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. U.S. Pat. No. 5,466,254, CORONARY SINUS LEAD WITH ATRIAL SENSING CAPABILITY, by Helland, which is hereby incorporated herein by reference, contains a description of a coronary sinus lead.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
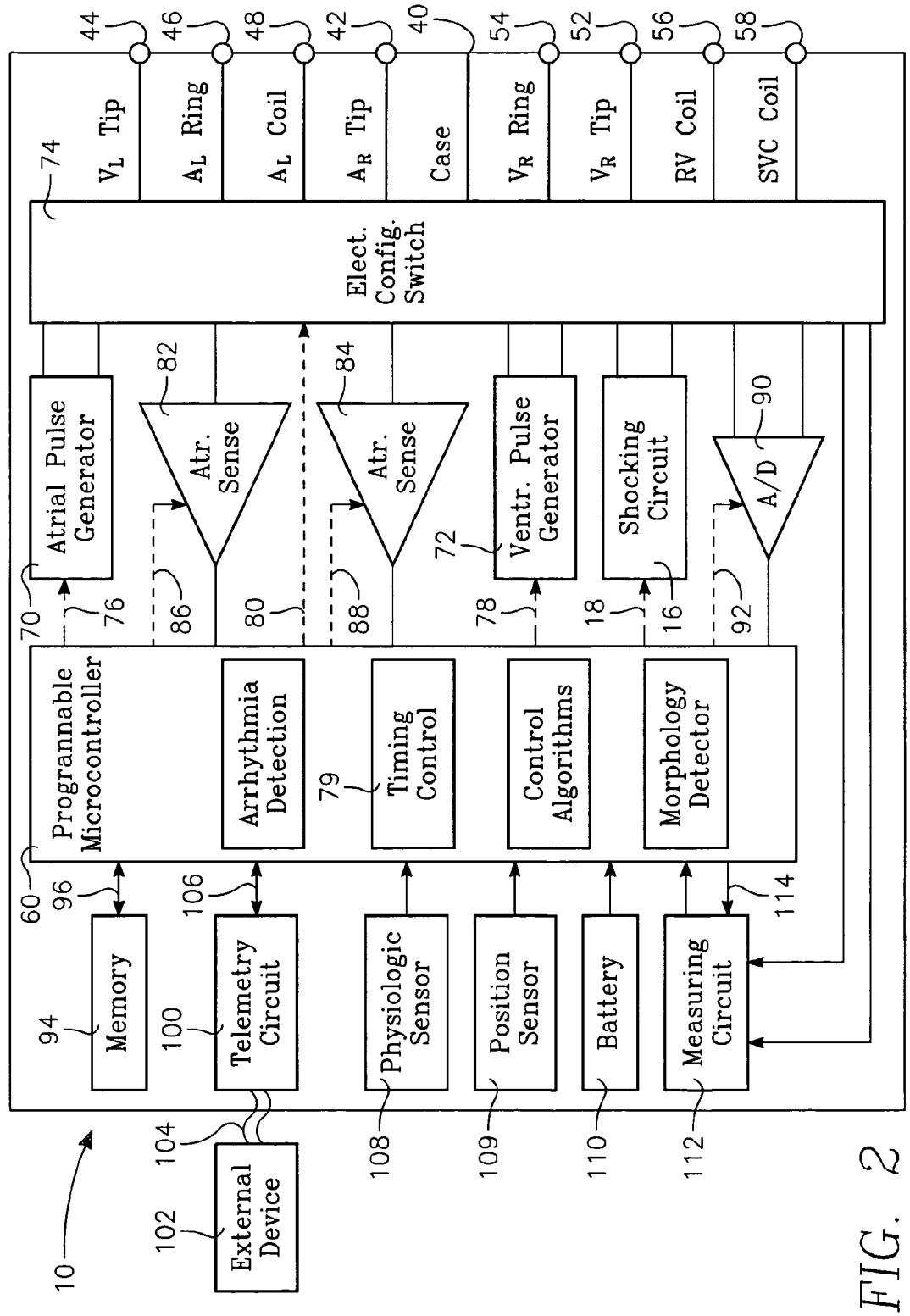
FIG. 2 illustrates a simplified block diagram is shown of the multi-chamber implantable stimulation device in accordance with an embodiment of the present invention.

FIG. 2 illustrates a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22 and a right atrial ring ($A_R$ RING) electrode 43 adapted for connection to right atrial ring electrode 23. To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively. To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks, collectively referred to as "tiered therapy"). Similar capabilities would exist on the atrial channel with respect to tachycardias occurring in the atrium. These would be atrial tachycardias (AT), more rapid atrial tachycardias (Atrial Flutter) and atrial fibrillation (AF).

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller may include a capture-based tachycardia detection unit, which operates to detect a tachycardia based on loss of capture of pacing pulses. In the primary example described herein, the tachycardia detection unit operates to detect AF based on loss of capture of atrial pacing signals during preventive overdrive pacing in the atrium. Accordingly, the capture-based tachycardia detection unit is used in conjunction with a preventive overdrive pacing unit for controlling overdrive pacing of the heart. One particularly effective overdrive pacing technique, referred to herein as dynamic atrial overdrive (DAO) pacing, is described in U.S. Pat. No. 6,519,493 to Florio et al., entitled METHODS AND APPARATUS FOR OVERDRIVE PACING HEART TISSUE USING AN IMPLANTABLE CARDIAC STIMULATION DEVICE, which is incorporated by reference herein. With DAO, the overdrive rate is controlled to remain generally uniform and, in the absence of a tachycardia, is adjusted upwardly or downwardly only occasionally. Dynamic overdrive techniques are also applicable to the ventricles. Exemplary dynamic ventricular overdrive (DVO) techniques are described in U.S. patent applications: 1) Ser. No. 10/456,060 to Park et al., entitled SYSTEM AND METHOD FOR DYNAMIC VENTRICULAR OVERDRIVE PACING, filed Jun. 6, 2003, Ser. No. 10/456,058, entitled SYSTEM AND METHOD FOR DYNAMIC VENTRICULAR OVERDRIVE PACING, Jun. 6, 2003, which applications are also incorporated herein by reference. In one example, the overdrive pacing unit operates continuously in the absence of a tachycardia so as to reduce the likelihood of the onset of a tachycardia. In other examples, preventive overdrive pacing is suspended while the patient is asleep. It is also suspended when the patient is in a tachycardia that has resulted in the enabling of the Automatic Mode Switch algorithm. In any case, if a tachycardia is detected during preventive overdrive pacing by the tachycardia detection unit, an ATP unit is activated to deliver antitachycardia pacing to the heart in an effort to terminate the tachycardia.

The ATP unit may administer ATP in accordance with any of a variety of ATP techniques. Exemplary patents describing ATP techniques include U.S. Pat. No. 6,101,414, to Mark Kroll, entitled METHOD AND APPARATUS FOR ANTI-TACHYCARDIA PACING WITH AN OPTIMAL COUPLING INTERVAL, and U.S. Pat. No. 5,431,689 to Weinberg et al., entitled IMPLANTABLE STIMULATION SYSTEM AND METHOD FOR TERMINATING CARDIAC ARRHYTHMIAS, which are both incorporated by reference herein. Tachycardia may be detected during preventive overdrive pacing based, for example, upon detection of a true loss of capture of a preventive overdrive pacing pulse or upon detection of a loss of capture of a backup pulse subsequent to a PAC.

To detect loss of capture, the microcontroller also includes an automatic capture detection unit for detecting an evoked response from the heart in response to an applied stimulus. The capture detection unit verifies capture of both primary pacing pulses and any subsequent backup pulses. Capture occurs when an electrical stimulus applied to the heart is of sufficient energy to depolarize the cardiac tissue, thereby causing the heart muscle to contract. The capture detection unit detects a depolarization signal during a window following a stimulation pulse, the presence of which indicates that capture has occurred. Capture detection is performed on a beat-by-beat basis. If a primary pulse is not captured, a backup pulse unit delivers a backup pulse at a maximum pulse magnitude. The capture detection unit also detects whether the backup pulse captures.

Also included is a stimulation threshold search unit for automatically determining the current capture threshold of the patient, i.e. the minimum output sufficient to evoke capture, so that the output or pulse magnitude can be reset properly. This is commonly reported in terms of pulse amplitude as this is one of the programmable output parameters. While preventive overdrive pacing is performed, a stimulation search is automatically performed in circumstances wherein a primary pacing pulse is not captured but the backup pulse is captured. (If both the overdrive pulse and the backup pulse are not captured, ATP is instead activated.) Also, preferably, a capture threshold search is performed periodically to update the capture threshold regardless of whether any loss of capture is detected. Such capture threshold searches are preferably performed every eight hours. Typically, a capture threshold search begins at a desired starting point (either a high energy level or the level at which capture is currently occurring) and decreases the energy level until capture is lost. It then increments the output in 0.125 Volt steps until capture is restored. The value at which capture is restored is known as the capture threshold. Thereafter, a working margin or a safety margin is added to the capture threshold to yield a new pulse magnitude. A safety margin is a fixed multiple of the measured threshold. A working margin is a fixed value, e.g. 0.25 Volts above the measured threshold. In one implementation, the safety margin is provided by the high output backup pulse. The delivered output associated with the primary pulse is simply a working margin above the measured capture threshold.

Various techniques for implementing capture verification of atrial pacing pulses (i.e. atrial AutoCapture) are set forth in U.S. Pat. Nos. 6,434,428 to Sloman et al.; 6,311,089 to Mann et al.; 6,285,908 to Mann et al.; 6,263,244 to Mann et al.; 6,259,950 to Mann et al.; 6,243,606 to Mann et al.; and 6,101,416 to Sloman, which are incorporated herein by reference. Capture verification of ventricular pulses is described in U.S. Pat. No. 6,456,882 to Schloss; U.S. Pat. No. 6,456,881 to Bornzin et al.; and U.S. Pat. No. 6,345,201 to Sloman, et al., which are also incorporated herein by reference. See also U.S. Pat. No. 4,686,988 (Sholder); U.S. Pat. No. 4,969,467 (Callaghan et al.); and U.S. Pat. No. 5,350,410 (Mann et al.), which patents are hereby incorporated herein by reference. A technique for implementing automatic capture verification during overdrive pacing is described in U.S. patent application Ser. No. 10/138,438, filed May 2, 2002, of Bradley et al., entitled METHOD AND APPARATUS FOR PROVIDING ATRIAL AUTOCAPTURE IN A DYNAMIC ATRIAL OVERDRIVE PACING SYSTEM FOR USE IN AN IMPLANTABLE CARDIAC STIMULATION DEVICE, which is incorporated herein by reference.

The microcontroller also includes a PAC detection unit 109 and a PAC response unit. The PAC detection unit detects PACs and the PAC response unit provides a pacing protocol for responding to the PAC. An exemplary PAC response protocol is described in U.S. Pat. No. 5,978,709 to Begemann et al., entitled PACEMAKER SYSTEM WITH IMPROVED TECHNIQUES FOR PREVENTING AND SUPPRESSING ATRIAL ARRHYTHMIAS, which is incorporated herein by reference.

Although shown as being components of the microcontroller, any or all of capture-based tachycardia detection unit, overdrive pacing unit, ATP unit, capture detection unit, stimulation threshold search unit, PAC detection unit, PAC response unit, and backup pulse unit could be instead implemented as separate components. Also, depending up on the particular component and the particular implementation, individual components may be configured to apply to the ventricles, the atria, or in some cases both.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Other pacing parameters include base rate, rest rate and circadian base rate.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. In the one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. (V-V delay is typically used in only connection with independently programmable RV and LV leads for biventricular pacing.)

While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, respiration rate and/or minute ventilation, pH of blood, ventricular gradient, etc. Any sensor may be used which is capable of sensing a physiological parameter that corresponds to the exercise state of the patient.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices. As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate antitachycardia pacing therapy or electrical shock therapy to the heart aimed at terminating the detected arrhythmia. To this end, the microcontroller 60 further controls a shocking circuit by way of a control signal. The shocking circuit generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are of relatively low to moderate energy level (so as to minimize the current drain on the battery) and are usually between 5 to 20 joules. Typically, cardioversion shocks are synchronized with an R-wave. Defibrillation shocks are generally of moderate to high energy level (i.e., corresponding to thresholds in the range of 15 to 40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

A position sensor 109, such as a 3D accelerometer is included to determine the patient's position, and thus posture. An example system and method for determining patient posture is disclosed in U.S. patent application Ser. No. 10/329,233, by the present inventor, filed Dec. 23, 2002, entitled SYSTEM AND METHOD FOR DETERMINING PATIENT POSTURE BASED ON 3-D TRAJECTORY USING AN IMPLANTABLE MEDICAL DEVICE, and in U.S. patent application Ser. No. 10/328,642, by the present inventor, filed Dec. 23, 2002, entitled SYSTEM AND METHOD FOR DETERMINING PATIENT POSTURE BASED ON 3-D TRAJECTORY USING AN IMPLANTABLE MEDICAL DEVICE, both herein incorporated by reference in their entireties. In some embodiments the position sensor may be located external to the housing 10. In other embodiments, the position sensor 109 may be located internal to the housing 10 and may be part of the physiological sensor 108 as shown in U.S. Pat. No. 6,658,292, by Kroll et al., entitled DETECTION OF PATIENT'S POSITION AND ACTIVITY STATUS USING 3D ACCELEROMETER-BASED POSITION SENSOR, issued Dec. 2, 2003, herein incorporated by reference in its entirety. Any sensor may be used which is capable of sensing position, such as a magnetic field sensor (not shown), for example a GMR sensor, or other positioning sensor/system for use in determining/confirming a patient's position and/or posture.

As discussed further below, instead of using 3D accelerometer measurements to compensate pacing for activity level, the accelerometer values are used to check the validity of heart failure surrogate parameters (discussed below with reference to FIG. 4) from the evoked response of the heart (shown in FIG. 3).

Figure 3:
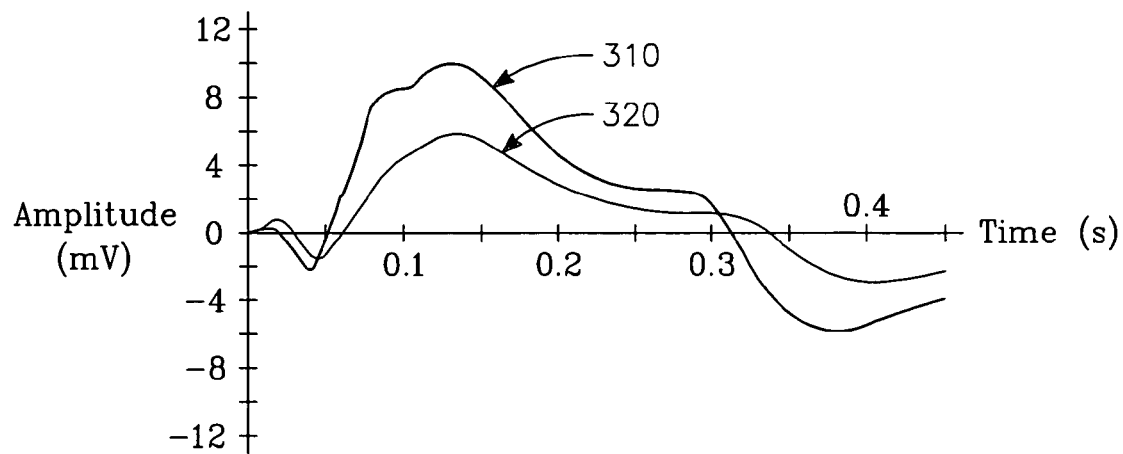
FIG. 3 is a graphical illustration of empirical data showing an overlay of a normal ventricular evoked response and a ventricular evoked response of a failing heart.

FIG. 3 is an overlay of two EGMs of ventricular evoked responses. An IEGM or intracardiac electrogram is a graphic depiction of the electrical signal emitted by active cardiac tissue and recorded through electrodes placed on or within the heart. The graphical depiction is sometimes referred to simply as an electrogram or EGM. FIG. 3 is a graphical illustration of empirical data of a normal ventricular evoked response 310 and a ventricular evoked response 320 of a failing heart. Generally, the ventricular evoked response 320 of the failing heart has a lower amplitude and slower evoked response. As discussed above, in certain types of heart failure, such as congestive heart failure or CHF, this change will occur over time. Thus, analysis of the trend of the evoked response over time is useful in predicting heart failure. Evoked response parameters, shown in FIG. 4, can be employed to quantify the evoked response for use in heart failure analysis.

Figure 4:
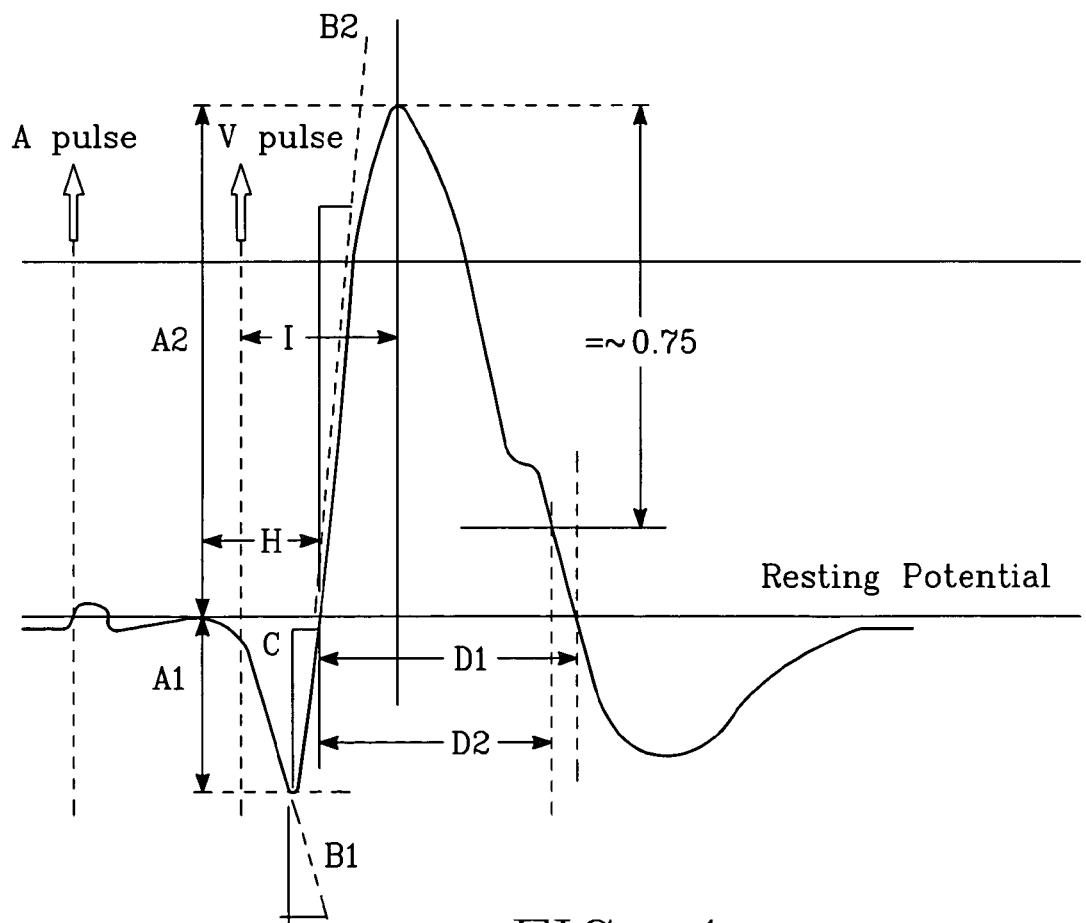
FIG. 4 shows a simplified graphical illustration of a ventricular evoked response of a heart.

FIG. 4 shows a simplified graphical illustration of a ventricular evoked response 300 of a heart. This illustration shows parameters A1, A2, B1, B2, C, D1, D2, H, and I which are possible heart failure surrogate candidates. Changes in the one or more parameters can indicate impending heart failure. Parameter A1 is the peak negative amplitude of the evoked response 300. A2 is the peak positive amplitude or maximum of T wave amplitude. B1 is the peak negative slope and B2 is the peak positive slope. It is possible to use a parameter $D_{max}$ (not shown in FIG. 4). $D_{max}$ is defined as the maximum among the slopes every 25 milliseconds during the peak positive slope B2.

Referring to FIG. 4, the parameter C is the paced depolarization integration or PDI. The paced depolarization integration is inversely related to intraventricular conduction velocity and directly related to ventricular mass. Thus, the paced depolarization integration is useful for assessing optimal AV delay and progression of heart failure. Because the blanking period does not allow a full intracardiac electrogram immediately after V-pulse, it is possible to use a partial intracardiac electrogram between zero-crossing (from negative to positive) and the zero-crossing minus a fixed time. The fixed time may be 10% of zero-crossing time minus the time of the placed depolarization integration valley.

As shown in FIG. 4, the parameter D1 is the evoked response duration. D1 is the clinical equivalent of action potential duration or APD. D1 may be useful in detecting alternans and in assessing the electrical property of cell restoration. D2 is 75% of the evoked response duration. The parameter H is the time at zero-crossing and the parameter I is the time to the maximum peak. The parameters shown in FIG. 4 are one simple way to compare IEGMs collected chronologically. More complicated 2-D comparison is possible As discussed above, the evoked response morphology can change when posture changes. For example, if the posture changes from supine to upright, a significant change in amplitude has been observed. Similarly, a change from supine to a side posture or to prone can cause a change in evoked response morphology not attributable to heart failure. Thus, detection of an evoked response in a different posture during the rest state could lead to a false indication of heart failure.

Figure 5:
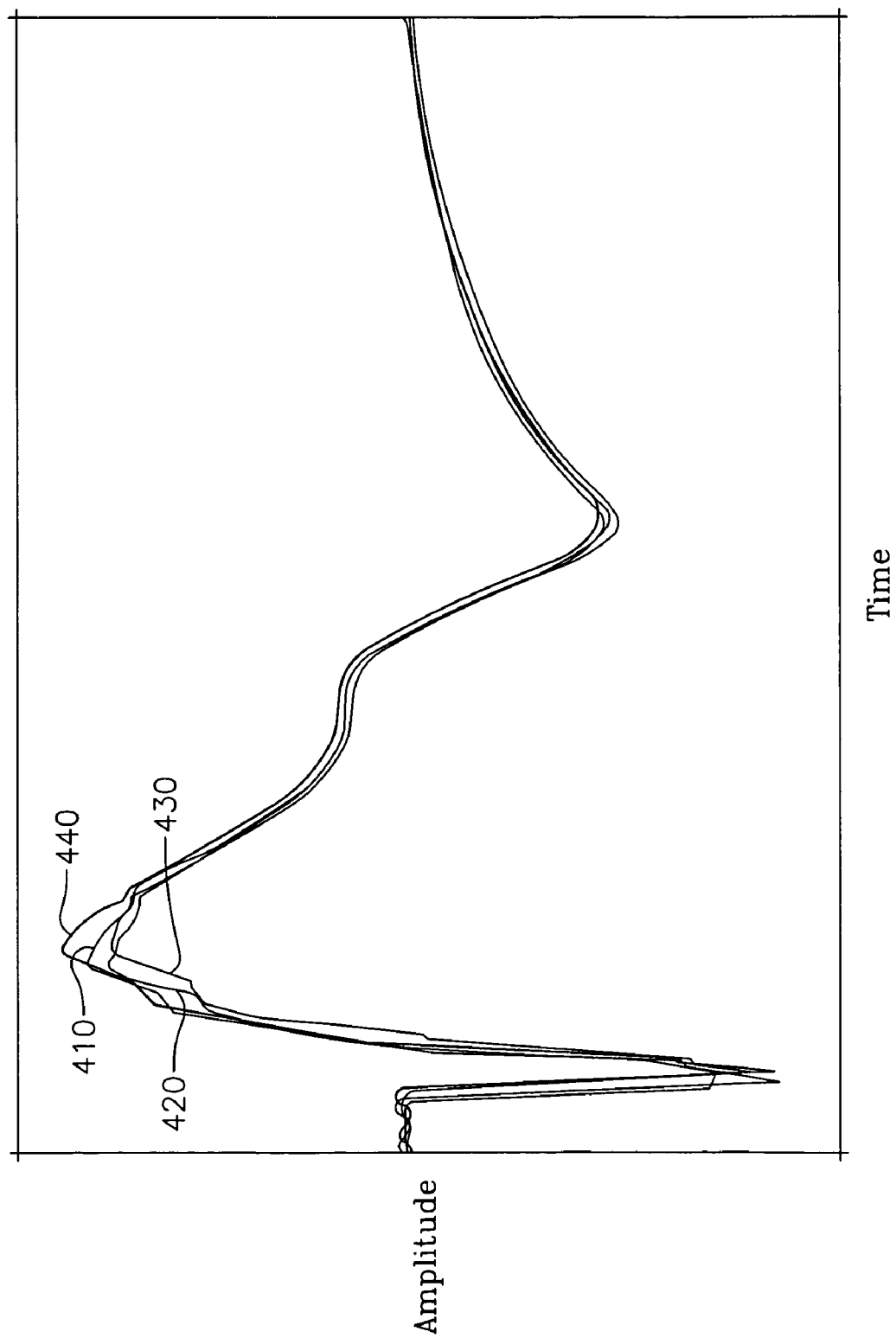
FIG. 5 is a graphical illustration of empirical data showing an overlay of evoked responses measured in the rest state for right side, prone, supine, and sitting postures.

FIG. 5 is a graphical illustration of empirical data showing an overlay of evoked responses measured in the rest state for right side 410, prone 420, supine 430 and sitting 440 postures. As is shown, the curves for the evoked response differs for different postures. For example, in terms of the maximum amplitude parameter A1 discussed above, the sitting curve 440 indicates the highest maximum amplitude A1, while supine 430 and prone 420 show much lower maximum amplitudes A1. The curve for the right side 410 has a maximum amplitude A1 between that of sitting 440 and supine 430. The other parameters, discussed above could be used to quantify the differences between the evoked response curves for the different postures.

A posture template may be stored indicating the posture of the patient, i.e. supine, prone, left side, right side, sitting, etc., or variations, associated with the a stored evoked response curve, and/or one or more evoked response parameters. The posture template may be stored as a position template, for example $x_T$, $y_T$, and $z_T$, or other position coordinates.

Figure 6:
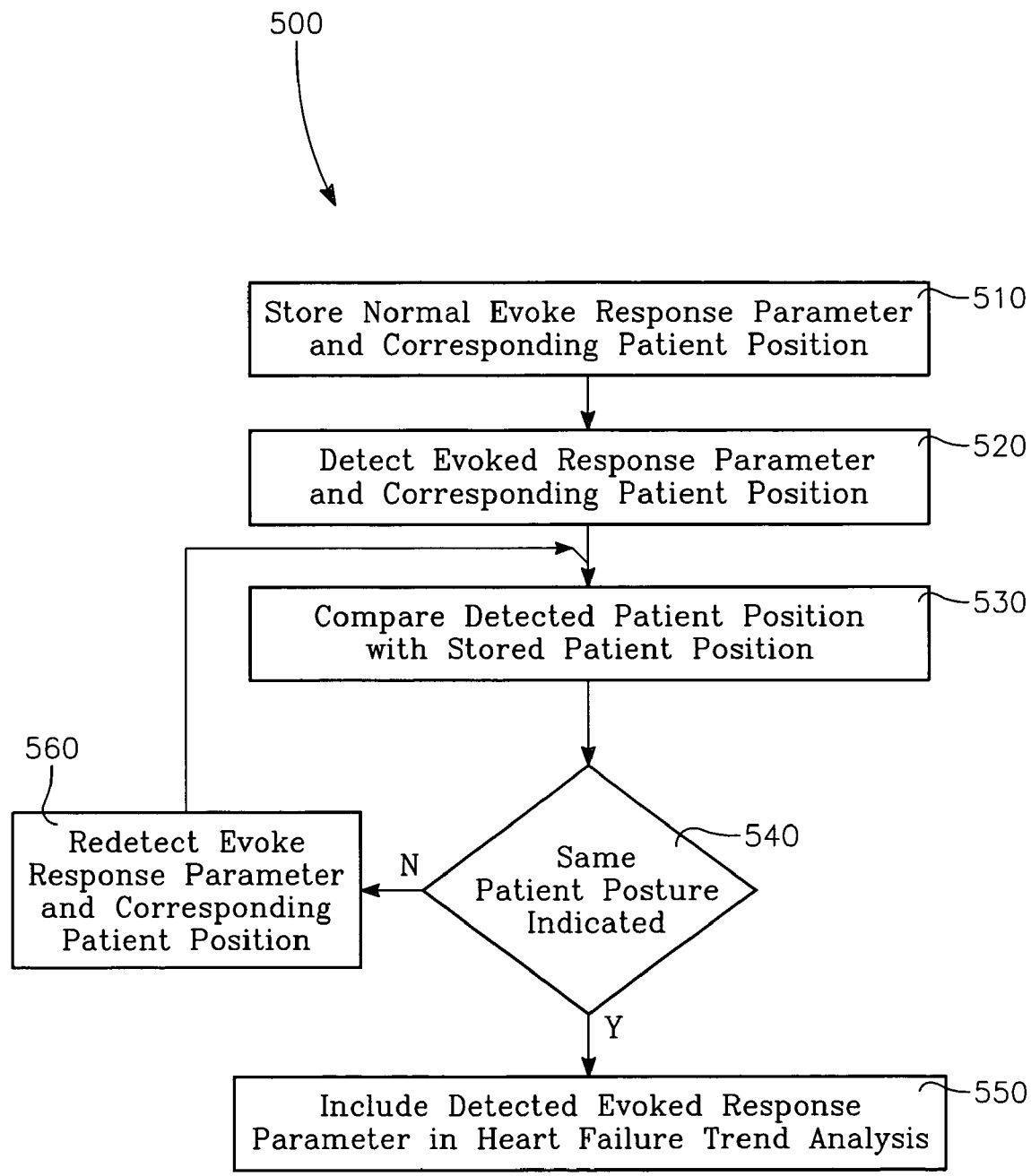
FIG. 6 shows a flow chart in accordance with a possible implementation of the present invention.

FIG. 6 shows a flow chart 500 in accordance with one possible implementation. A normal evoked response parameter of a patient along with the corresponding patient position is stored 510. The storing of the normal evoked response parameter may include storing several evoked response parameters, such as those discussed above or other evoked response parameters, or it may include storing the entire intracardiac electrogram or IEGM of the evoked response. The IEGM may be processed to extract the desired parameters. The extraction of the parameters may be performed by the implantable pacemaker device, or by the programmer. The term evoked response as used herein includes the evoked response parameter(s) and/or the IEGM. The patient position is stored as a template value corresponding to the normal evoked response. The patient position template value may be stored as $x_T$, $y_T$, and $z_T$, for example. The patient position template value may be derived from or supplied by a position sensor such as a three-dimensional accelerometer (discussed above with reference to FIG. 2).

To detect heart failure in a patient, an evoked response and the corresponding patient position is detected 520. The detected patient position and the stored patient position corresponding to the normal evoked response are compared 530. If the same patient posture is indicated at 540, the detected evoked response is included heart failure analysis at 550, which may include heart failure trend analysis. Typically, several readings of the evoked response are averaged to remove the effect of respiration, which can modulate the shape of the evoked response waveform. Analysis of the trend of the evoked response over a period of time, i.e. hours, days, weeks, months, can indicate when heart failure is imminent. If heart failure is imminent, pacing therapy may be administered by the pacemaker, such as biventricular pacing to treat congestive heart failure.

The evoked response is usually sampled during a rest state, such as at night when the patient is sleeping. Thus, a timer may be set for a period such as 8 hours, which provides a window for sampling the evoked response during the rest state. In some implementations, the sampling may be performed periodically during the rest state until the patient posture matches the template posture. Thus, in one optional implementation shown in box 560, if the same patient posture is not indicated in box 540, the evoked response and corresponding patient position is re-detected at 560 and the resulting detected patient posture and stored patient position is compared 530. The evoked response is included in heart failure analysis at 550 if the same patient position is then indicated at 540.

It is important to note that in some implementations, the evoked response need not be detected until after the detection of the patient position. If the same patient position is indicated by comparison with the stored patient position, the evoked response can then be detected. Thus, in FIG. 6 the evoked response may be detected after the same posture is indicated at 540 rather than along with detection of the patient position in box 520.

Figure 7:
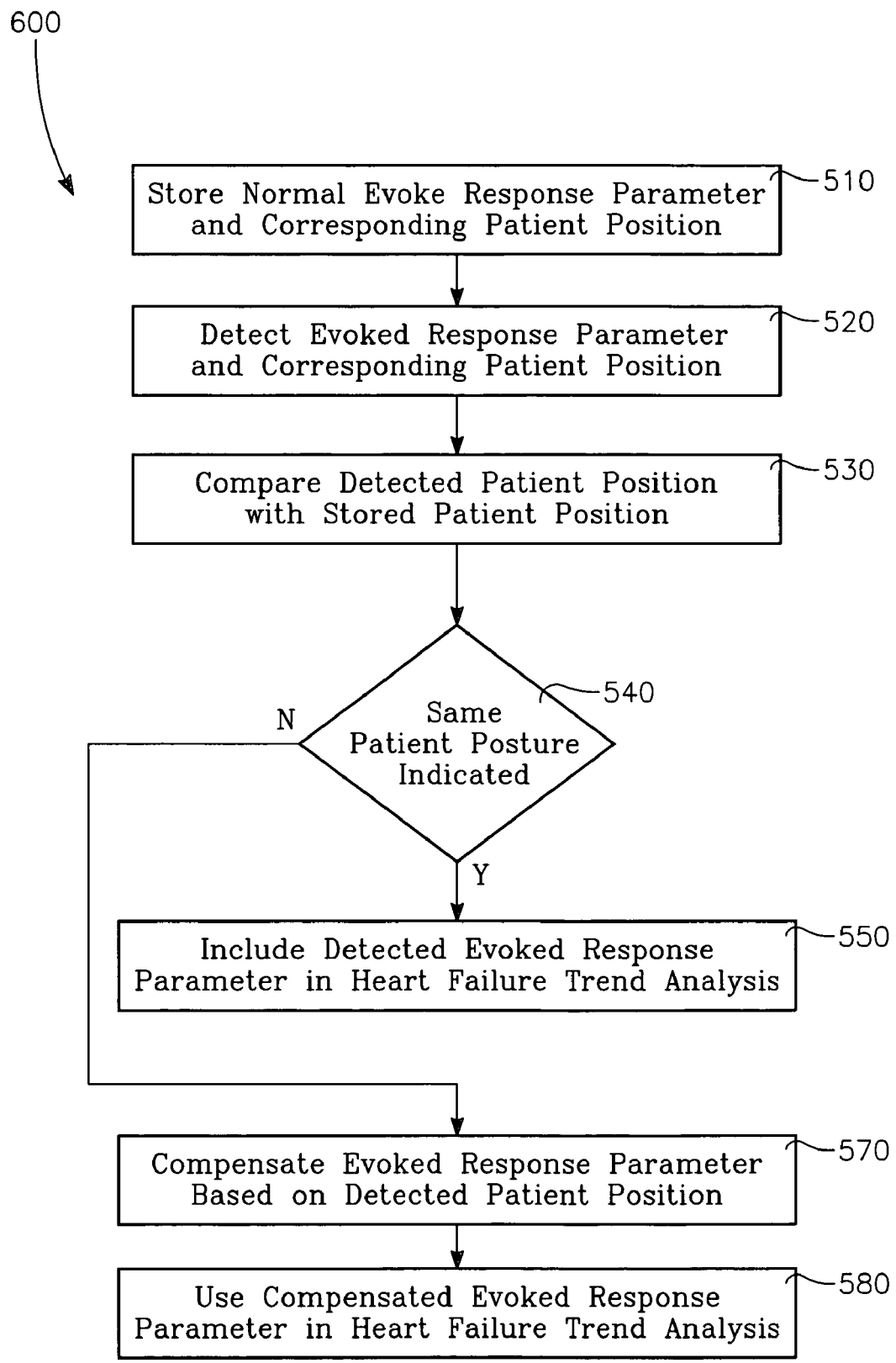
FIG. 7 shows a flow chart in accordance with a possible implementation of the present invention.

FIG. 7 shows a flow chart 600 in accordance with an alternate implementation. Shown at boxes 570 and 580, if the same patient posture is not indicated at 540, the evoked response may be compensated 570 to account for the different patient posture. The compensated evoked response may be used in heart failure analysis 580 in place of the detected evoked response.

Referring to FIGS. 6 and 7, in yet a further implementation, not specifically shown in FIG. 6 or 7, if the re-detection of the patient position at 560 does not yield the same patient posture, for example within a designated time period, such as the rest state period, the evoked response may be compensated based on the detected patient position 570. The compensated evoked response may then be used in heart failure analysis after re-detection fails to yield a same patient posture at 540.

Figure 8:
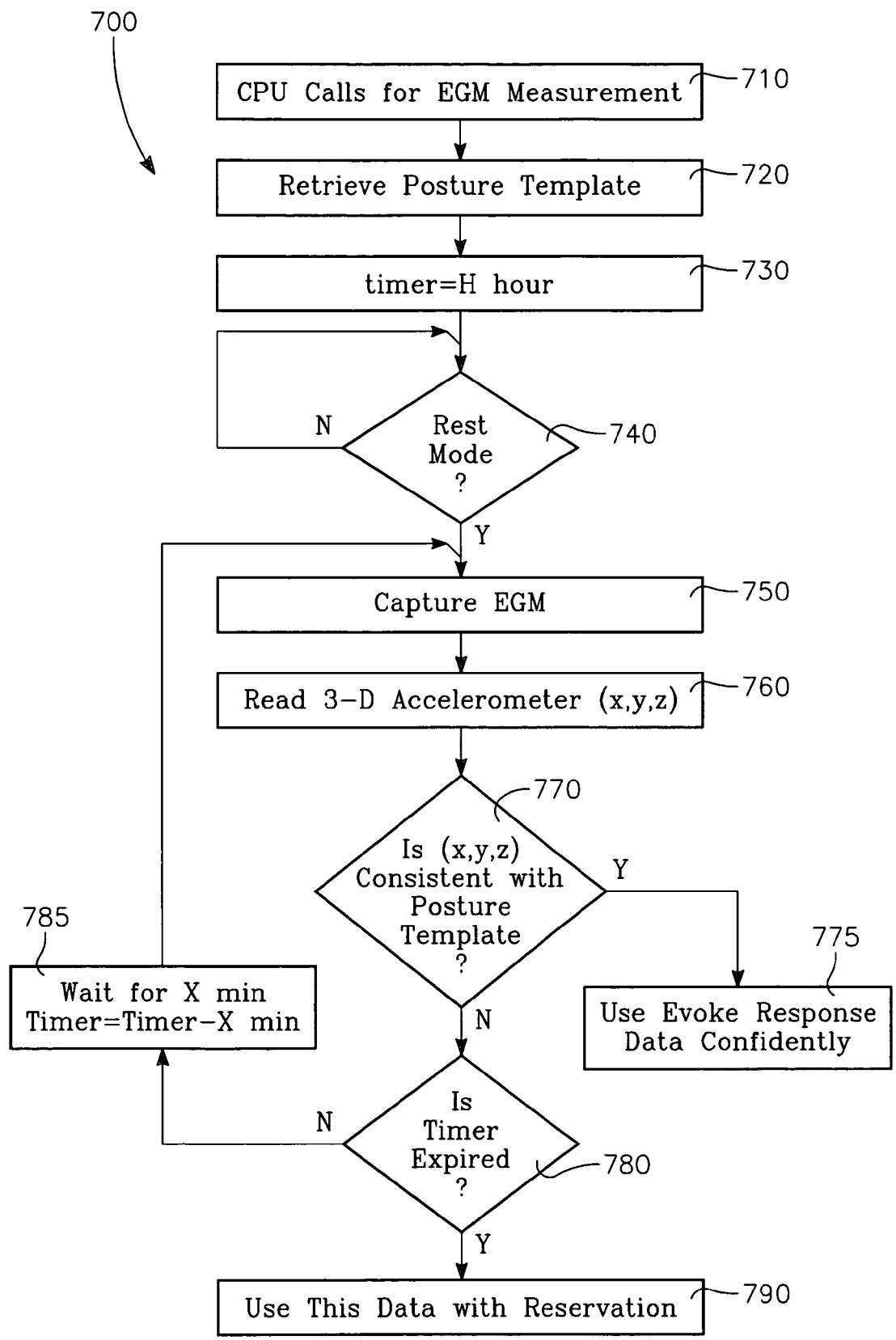
FIG. 8 shows a flow chart in accordance with a possible implementation of the present invention.

FIG. 8 shows a flow chart 700 in accordance with a possible implementation of the present invention. In this flow chart a processor calls for an EGM measurement 710. Thereafter, a posture template is retrieved 720 and a timer is set 730. The evoked response is usually sampled during a rest state, such as at night when the patient is sleeping. Thus, a timer may be set for 8 hours, which provides a window for sampling the evoked response during rest the rest state. If it is verified that the patient is in rest mode 740, the EGM is captured 750 and a 3-D accelerometer is read 760 to determine position, for example the x,y,z coordinates. If the position is consistent with the posture template at 770, the evoked response data is used confidently in heart failure analysis 775.

If the position data is not consistent with the retrieved posture template at 770 and the timer is not expired at box 780, wait a time period X, subtract the expired time X from the timer 785 and recapture the EGM 750, read the 3-D accelerometer 760, and determine if the 3-D accelerometer reading is consistent with the retrieved posture template at 770.

If the time expires at 780 without a reading of patient position that is consistent with the retrieved position template, the evoked response data is used with reservation 790. The evoked response data may be weighted or compensated prior to use in heart failure analysis, or simply discard as unreliable. In one implementation, if the timer expires before a position reading consistent with the retrieved posture template is found, the best EGM, captured when the patient was in a position close to the template posture, may be used for heart failure analysis.

Unlike the conventional use of 3D accelerometer measurements in compensating heart pacing for activity level, certain embodiments provide a means for ensuring the validity of heart surrogate parameters from an evoked response using a 3D accelerometer queue for heart failure analysis. This may include a means for storing a template posture based on 3D accelerometer measurement corresponding to a baseline evoked response parameter, and, for periodically comparing a current posture measurement from the 3D accelerometer with the template posture to verify whether an evoked response parameter is valid for use in heart failure trend analysis.

If the IEGM morphology or parameter is measured when the body posture is the same, the IEGM morphology/parameter may be used more reliably for heart failure trend analysis. In comparing the template values to the detected position values, the detected position values and the position template values should be within some threshold distance to indicate a same posture. If the detected position is within a threshold distance to a position template value, the IEGM parameter may be used for comparison with the IEGM parameter(s) associated with that posture. If several position templates are stored, i.e. prone, supine, sitting, standing, laying on side, etc., the detected IEGM parameter may be included with a stored IEGM parameter with the same or similar posture for trend analysis.

Furthermore, it is possible to compare the trends of the IEGM parameters across different position templates. For example, if some readings are from the supine posture and others are from the prone posture, the trend of the IEGM parameters for the supine posture may be analyzed along with the trend of the IEGM parameters for the prone posture, and used to indicate heart failure. Thus, the trends of the IEGM parameter(s) for different postures may be used separately or in combination to indicate heart failure.

As can be appreciated a wide variety of techniques can be implemented consistent with the principles of the invention and no attempt is made herein to describe all possible embodiments and implementations. Although described primarily with reference to congestive heart failure, the principles of the invention are applicable to other implanted cardiac stimulation devices as well, such as pacemakers without congestive heart failure therapy capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. An implantable cardiac pacemaker device for detecting heart failure comprising:
   a three-dimensional accelerometer; and
   a means for ensuring the validity of heart failure surrogate parameters from an evoked response using the three-dimensional accelerometer.

2. The device of claim 1 wherein the means for ensuring the validity of the heart surrogate parameters comprises:
   a) a means for storing a posture template based on the three-dimensional accelerometer measurement, the posture template corresponding to a baseline evoked response parameter; and
   b) a means for periodically comparing a current posture based on a three-dimensional accelerometer measurement with the posture template to verify whether an evoked response parameter corresponding to the current posture is valid for use in heart failure trend analysis.

3. The device of claim 2 further comprising a means for compensating the evoked response parameter corresponding to the current posture if the current posture indicates a posture different from the posture template.

4. The device of claim 2 wherein the means for storing the posture template based on the three-dimensional accelerometer measurement comprises a means for storing multiple posture templates and corresponding evoked response parameters, each of the multiple posture templates corresponding to a different body posture.

5. A method for detecting heart failure comprising:
   a) capturing an intracardiac electrogram of an evoked response;
   b) detecting a three-dimensional posture corresponding with the captured intracardiac electrogram;
   c) retrieving a three-dimensional posture template;
   d) comparing the detected three-dimensional posture and the three-dimensional posture template; and
   e) using the captured intracardiac electrogram for heart failure trend analysis if the comparison of the detected three-dimensional posture and the three-dimensional posture template indicates a same posture.

6. The method of claim 5 wherein detecting the three-dimensional posture comprises reading an input from a three-dimensional accelerometer.

7. The method of claim 5 further comprising re-capturing the intracardiac electrogram and re-detecting the three-dimensional posture corresponding with the re-captured intracardiac electrogram if the comparison of the detected three-dimensional posture and the retrieved three-dimensional posture template indicates a different posture.

8. The method of claim 7 further comprising periodically re-capturing the intracardiac electrogram and re-detecting the three-dimensional posture corresponding with the re-captured intracardiac electrogram if the comparison of the detected three-dimensional posture and the retrieved three-dimensional posture template indicate a different posture.

9. The method of claim 5 further comprising verifying rest mode prior to capturing the intracardiac electrogram.

10. The method of claim 5 further comprising omitting the intracardiac electrogram from heart failure trend analysis if the comparison of the detected three-dimensional posture and the three-dimensional posture template indicates a different posture.

11. The method of claim 5 wherein detecting a three-dimensional posture corresponding with the captured intracardiac electrogram comprises detecting x, y, and z values, and wherein retrieving a three-dimensional template comprises retrieving stored $x_T$, $y_T$, and $z_T$ values, and wherein comparing the detected three-dimensional posture and the three-dimensional posture template comprises comparing the detected x, y, and z with the stored $x_T$, $y_T$, and $z_T$, and wherein using the captured intracardiac electrogram comprises including the captured intracardiac electrogram in heart failure analysis if the comparison of the detected x, y, and z and the stored $x_T$, $y_T$, and $z_T$ indicates a same posture.

12. The method of claim 5 wherein capturing an intracardiac electrogram comprises capturing a ventricular evoked response.

13. The method of claim 5 wherein using the captured electrocardiogram for heart failure analysis comprises averaging several captured electrocardiograms.

14. The method of claim 5 wherein retrieving the three-dimensional posture template comprises retrieving three-dimensional posture templates for a plurality of different postures.

15. The method of claim 14 wherein using the captured electrocardiogram for heart failure analysis comprises evaluating multiple trends associated with multiple different postures.

16. A method for detecting heart failure comprising:
  a) storing a patient position associated with an evoked response parameter;
  b) detecting a subsequent evoked response parameter;
  c) detecting a patient position corresponding to the detected evoked response;
  d) comparing the detected patient position with the stored patient position; and
  e) including the detected evoked response parameter in heart failure trend analysis if the detected patient position indicates a same posture as the stored patient position associated with the normal evoked response.

17. The method of claim 16 wherein detecting the patient position corresponding to the detected evoked response parameter comprises detecting three-dimensional position data.

18. The method of claim 17 wherein detecting the patient position corresponding to the detected evoked response parameter comprises reading an input from a three-dimensional accelerometer.

19. The method of claim 17 further comprising storing a patient position corresponding to a normal evoked response parameter for multiple different postures, and wherein including the detected evoked response parameter in heart failure trend analysis comprises associating the detected evoked response parameter with the stored normal evoked response parameter having a detected stored patient position indicating a same posture as the stored normal evoked response parameter.

20. The method of claim 19 further comprising evaluating multiple trends associated with multiple different postures.

21. The method of claim 17 further comprising compensating the detected evoked response parameter prior to including the detected evoked response parameter in heart failure trend analysis if the detected patient position indicates a different posture than the stored patient position associated with the normal evoked response.

22. The method of claim 17 wherein storing a normal evoked response parameter of a patient comprises storing a ventricular evoked response parameter.

23. The method of claim 17 wherein including the detected evoked response parameter comprises averaging a plurality of readings of the evoked response parameter.

* * * * *